(12) United States Patent
Allmendinger et al.

(10) Patent No.: US 8,897,525 B2
(45) Date of Patent: Nov. 25, 2014

(54) MULTISEGMENT PICTURE RECONSTRUCTION FOR CARDIO CT PICTURES

(75) Inventors: Thomas Allmendinger, Forchheim (DE); Bernhard Schmidt, Fürth (DE)

(73) Assignee: Siemens Aktiengesellschaft, Munich (DE)

( * ) Notice: Subject to any disclaimer, the term of this patent is extended or adjusted under 35 U.S.C. 154(b) by 441 days.

(21) Appl. No.: 13/069,438

(22) Filed: Mar. 23, 2011

(65) Prior Publication Data

US 2011/0243419 A1    Oct. 6, 2011

(30) Foreign Application Priority Data

Mar. 30, 2010    (DE) .......................... 10 2010 013 360

(51) Int. Cl.
| | |
|---|---|
| *G06K 9/00* | (2006.01) |
| *G06T 5/50* | (2006.01) |
| *G06T 11/00* | (2006.01) |
| *G06T 5/00* | (2006.01) |
| *A61B 6/00* | (2006.01) |

(52) U.S. Cl.
CPC ....... *A61B 6/503* (2013.01); *G06T 2207/10081* (2013.01); *G06T 5/50* (2013.01); *G06T 11/005* (2013.01); *G06T 2207/30004* (2013.01); *G06T 5/003* (2013.01); *A61B 6/5264* (2013.01); *G06T 2211/412* (2013.01)
USPC .................... 382/131; 382/275; 378/4; 378/8

(58) Field of Classification Search
CPC ...... A61B 6/503; A61B 6/5264; G06T 5/003; G06T 5/50; G06T 11/005; G06T 2207/10081; G06T 2207/30004; G06T 2211/412
USPC .................................... 382/131, 275; 378/4, 8
See application file for complete search history.

(56) References Cited

U.S. PATENT DOCUMENTS 5,390,264 A * 2/1995 Ishihara et al. ............... 382/260
5,956,435 A * 9/1999 Buzug et al. .................. 382/283
(Continued)

FOREIGN PATENT DOCUMENTS

| | | |
|---|---|---|
| CN | 1615799 A | 5/2005 |
| CN | 1618403 A | 5/2005 |
| DE | 102007061935 A1 | 6/2009 |

OTHER PUBLICATIONS

Taguchi et al., "Image-domain motion compensated time-resolved 4D cardiac CT", Proc. of SPIE vol. 6510, 651016, (2007).*
(Continued)

*Primary Examiner* — Katrina Fujita
(74) *Attorney, Agent, or Firm* — Harness, Dickey & Pierce, P.L.C.

(57) ABSTRACT

A method for reconstructing picture data of a cyclically-moving object from measurement data is disclosed, with the measurement data being detected beforehand for a relative rotational movement between a radiation source of a computed tomography system and the object under examination during a plurality of movement cycles of the object under examination. In at least one embodiment, a first picture and a second picture are determined from the measurement data, with measurement data of different movement cycles being combined for reconstruction of the second picture into a measurement dataset to be used as the basis for the picture reconstruction. Difference information is computed by comparing the first picture with the second picture. Using the difference information, a result picture is computed from the first picture and the second picture.

16 Claims, 5 Drawing Sheets

(56) References Cited

U.S. PATENT DOCUMENTS

| | | | |
|---|---|---|---|
| 6,298,144 B1* | 10/2001 | Pucker et al. | 382/103 |
| 7,039,152 B2 | 5/2006 | Bruder et al. | |
| 7,221,728 B2* | 5/2007 | Edic et al. | 378/8 |
| 7,558,362 B2* | 7/2009 | Shechter et al. | 378/4 |
| 7,613,275 B2* | 11/2009 | Li et al. | 378/8 |
| 7,822,467 B2 | 10/2010 | Flohr et al. | |
| 2005/0195937 A1 | 9/2005 | Bruder et al. | |
| 2009/0161935 A1 | 6/2009 | Bruder et al. | |
| 2011/0142314 A1* | 6/2011 | Hsieh et al. | 382/131 |

OTHER PUBLICATIONS

Certified German Priority Application No. DE 10 2010 013 360.4 filed Mar. 30, 2010 (Not Yet Published).

Multi-slice CT in cardiac imaging: technical principles, clinical application and future developments Ohnesorge BBC, Flohr T, Reiser MF. Berlin, Germany: Springer Verlag; Book; 2002; DE.

High temporal resolution for multislice helical computed tomography Taguchi K., Anno H. Med. Phys. vol. 27 No. 5 pp. 861-872; Magazine; 2000; JP.

New Technical Developments in Multislice CT Part 2: Sub-Millimeter 16-Slice Scanning and Increased Gantry Rotation Speed for Cardiac Imaging. Forschr. Röntgenstr. 174, pp. 1022-1027, Flohr, t., Bruder H., Stierstorfer K., Simon J. Schaller S. Ohnesorge; Others; 2002; DE.

Heart rate adaptive optimization of spatial and temporal resolution for electrocardiogram-gated multislice spiral CT of the heart, J. Comput Assist Tomogr. 25, pp. 907-923, Flohr t, Ohnesorge B.; Others; 2001; DE.

Segment-Rekonstruktion: Ein neues Verfahren für die kardiologischeDiagnostik, Lembcke A. Rogalla P., Blobel J. VISIONS (ISSN 16-17-2876), 5, pp. 52-55; Others; 2001.

Improvement of temporal resolutions in ECG-gated CT-Coronary angiography using a 0,4 sec/Rotation multi-slice helical CT system Radiology 2001 (221) pp. 201-210 Anno H., Kato R., Katada K. et al.; Book.

Chinese Office Action and English translation thereof dated Mar. 5, 2014.

* cited by examiner

MULTISEGMENT PICTURE RECONSTRUCTION FOR CARDIO CT PICTURES

PRIORITY STATEMENT

The present application hereby claims priority under 35 U.S.C. §119 on German patent application number DE 10 2010 013 360.4 filed Mar. 30, 2010, the entire contents of which are hereby incorporated herein by reference.

FIELD

At least one embodiment of the invention generally relates to a method for reconstructing picture data of a cyclically-moving object under examination from measurement data, with the measurement data being detected beforehand during a relative rotational movement between a radiation source of a computed tomography system and the object under examination during a plurality of movement cycles of the object under examination.

BACKGROUND

Methods for scanning an object under examination with a CT system are generally known. Typical methods employed in such cases are orbital scans, sequential orbital scans with advance or spiral scans. Other types of scans which are not based on circular movements are possible, such as scans with linear segments for example. Absorption data of the object under examination is recorded from different recording angles with the aid of at least one X-ray source and at least one detector lying opposite said source and this absorption data or projections collected in this way are computed by means of appropriate reconstruction methods into picture slices through the object under examination.

For reconstruction of computed-tomographic pictures from X-ray CT datasets of a computed-tomography (CT) device, i.e. from the detected projections, what is known as a Filtered Back Projection (FBP) is used nowadays as the standard method. After the data has been recorded, a so-called "rebinning" step is executed in which the data generated with the beam spreading out in the form of a fan is rearranged such that it is available in a form such as would occur had the detector been hit by X rays arriving at the detector in parallel. The data is then transformed into the frequency range. A filtering is undertaken in the frequency range and subsequently the filtered data is back transformed. With the aid of the data sorted out and filtered in this way a back projection is then carried out onto the individual voxels within the volume of interest.

A disadvantage of this generally-known computation method lies in the fact that with a moving object under examination or an object under examination which moves at least in part, movement imprecision can arise in the picture, since during the period of a scanning process for the data which is needed for a picture a local displacement of the object under examination or of a part of the object under examination can occur, so that the basic data which leads to the picture does not all reflect spatially identical situations of the object under examination. This movement imprecision problem arises particularly acutely during the execution of cardio CT examinations of a patient for whom, as a result of the heart movement, a strong movement imprecision can occur in the area of the heart or for examinations in which relatively rapid changes in the object under examination are to be measured.

SUMMARY

In at least one embodiment of the invention, a method for reconstruction of CT pictures is demonstrated in which account is to be taken of the fact that a cyclically moving object under examination is present. In at least one embodiment, a corresponding control and processing unit, a CT system, a computer program and a computer program product are also to be demonstrated.

In at least one embodiment, a method is disclosed as well as a control and processing system, a CT system, a computer program and a computer program product. Advantageous embodiments and developments are the subject matter of subclaims.

In at least one embodiment of the inventive method for reconstruction from a measurement data of picture data of an object under examination moving in cycles, the measurement data is detected beforehand for a relative rotational movement between the radiation source of a computed tomography system and the object under examination during a plurality of movement cycles of the object under examination. A first picture and a second picture are determined from the measurement data. For reconstruction of the second picture measurement data of different movement cycles is combined into a measurement dataset to form the basis of the picture reconstruction. Difference information is calculated by a comparison between the first picture and the second picture and using the difference information a result picture is computed from the first picture and the second picture.

The object under examination or part of the object under examination moves cyclically or periodically. This means that consecutive movement cycles of the object under examination are present during which the object under examination completes more or less the same movement sequence. The movement of the object under examination—depending on the type of object under examination—can differ from cycle to cycle. An example of a cyclically moving object under examination is a beating heart.

The data is recorded so that data is not just recorded during one movement cycle of the object under examination, but instead the measurement extends over a number, i.e. at least two movement cycles. Preferably the data is recorded so that, for each segment of the object under examination for which a picture is to be recorded, a complete dataset for each of the number of movement cycles is available. I.e. it is possible for each of the number of movement cycles to reconstruct a CT picture from the protections measured for this.

First of all two pictures are determined. The second picture is characterized by the fact that the data on which its reconstruction is based does not just originate from one movement cycle; instead data from two or more movement cycles is used. This makes it possible to use data from a particular time-delimited section of the movement cycles and to increase the temporal resolution of the second picture by this. Various possibilities exist for the dataset to be used as the basis for the reconstruction of the first picture. The dataset can belong to precisely one of the number of movement cycles for example.

The first and the second picture are compared with one another. The result of this comparison, if necessary modified by further processing steps, is the difference information. This is used to compute the result picture which is produced from the first and the second picture. If the first and the second picture are linked to one another in a suitable manner, it is possible for the result picture to have the advantageous characteristics of both the first and also the second picture. In this case the advantages of the second picture especially relate to the good temporal resolution already explained.

In a development of at least one embodiment of the invention, for processing the result picture pixel-by-pixel a weighted sum is formed from the first picture and the second picture, with the weighting depending on the difference information. A pixel value of the result picture is thus produced as the sum of the corresponding pixel value of the first picture and the corresponding pixel value of the second picture, with one or both pixel values each being provided with a weighting factor. The difference information is included in the weighting factors.

It is especially advantageous if, for determining the first picture, at least a third and a fourth picture are reconstructed, with the third picture being reconstructed from data of the first movement cycle and the fourth picture from data of the second movement cycle, and the first picture is determined by forming the average from at least the third and the fourth picture. The individual pictures, i.e. the third and the fourth picture, thus relate to precisely one movement cycle. If data is recorded not only during two, but during a larger number of movement cycles, the first picture can be produced as the average of a larger number of individual pictures which each belong to another movement cycle. To form the mean value a simple or a weighted mean value from the individual pictures can be included. Since each of the individual pictures is based on data from a single movement cycle, the individual pictures have a bad temporal resolution. The result of forming the mean value for the first picture is advantageously that picture noise is reduced in relation to the individual pictures.

In one embodiment of the invention a multisegment reconstruction method is employed for determining the second picture.

It is especially useful for the first and the second picture to have temporal resolution which differs from one another; in particular the second picture can have a higher temporal resolution than the first picture. In this way the favorable temporal resolution of the second picture can be incorporated into the first image.

In one embodiment of the invention, a difference picture for calculating the difference information is determined by forming the difference between the first and the second picture pixel-by-pixel. Preferably this involves an absolute difference, i.e. a difference without taking account of the leading sign. It is also advantageous for the values of the difference picture to be set to zero below a first threshold value. This makes it possible to suppress noise in the difference picture. It is also possible to set the values of the difference picture above a second threshold value to the second threshold value or to another value. If both threshold values are used, the first threshold value should be smaller than the second threshold value. Finally it is especially advantageous for the difference picture to be subjected to lowpass filtering. This reduces sudden transitions in the difference picture. Finally the difference picture can be subjected to non-linear noise reduction before the lowpass filtering. The difference picture processed in the described manner can then be used to determine the result picture from the first and the second picture.

In at least one embodiment, using the difference information is to be able to provide location-dependent information about the degree of movement of the object under examination. Accordingly the two pictures from which the difference information is obtained by comparing the pictures can be selected differently. The only requirement is that their deviation from one another makes it possible to provide information about the movement. A further option for selecting the first and second picture is as follows:

In a development of at least one embodiment of the invention, the first picture is reconstructed from data of a first movement cycle, and for calculating the difference information, instead of the second picture, a fifth picture is included, with the fifth picture is being reconstructed from the data of a second movement cycle; a mean value picture is determined from the first and the fifth picture and the result picture is calculated from the mean value picture and the second picture using the difference information picture.

In at least one embodiment, the inventive control and processing unit is used for the reconstruction from measurement data of a CT system of picture data of an object under examination. It includes a program memory for storing program code, with the memory—if necessary as well as other program code—including program code which is suitable for executing a method of the type described above. In at least one embodiment, the inventive CT system includes such a control and processing unit. It can also include other components which are needed for recording measurement data for example.

In at least one embodiment, the inventive computer program has program code segments which are suitable for carrying out the method of the type described above when the computer program is executed on a computer.

In at least one embodiment, the inventive computer program product comprises program code segments stored on a computer-readable data medium which are suitable for carrying out the method of the type described above when the computer program is executed on a computer.

BRIEF DESCRIPTION OF THE DRAWINGS

The invention will be explained below in greater detail with reference to an example embodiment. The figures show.

DETAILED DESCRIPTION OF THE EXAMPLE EMBODIMENTS

Figure 1:
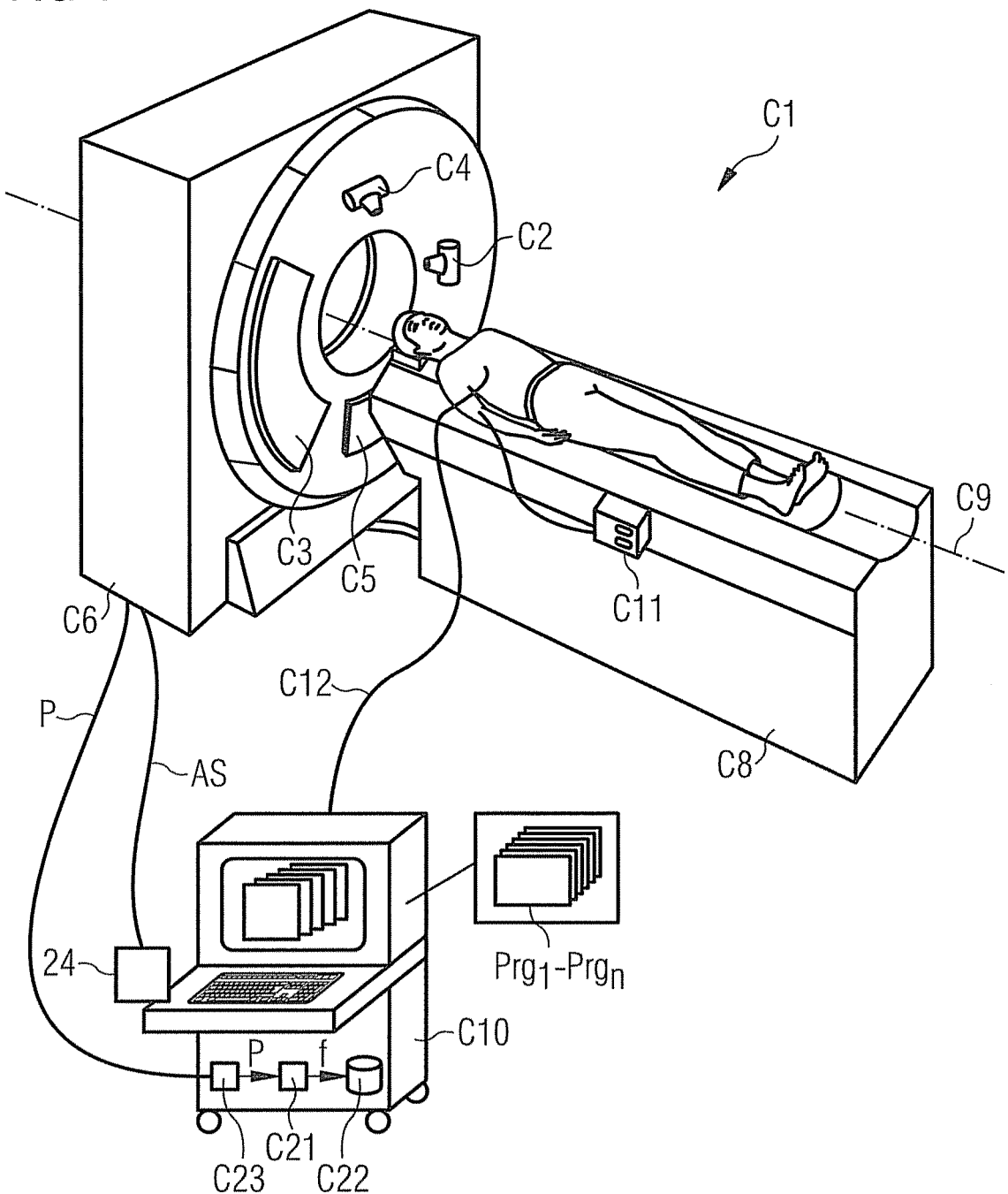
FIG. 1: a first schematic diagram of an example embodiment of a computed tomography system with a picture reconstruction component.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

FIG. 1 first shows a schematic diagram of a first computed-tomography system C1 with a picture reconstruction device C21. This involves what is known as a third-generation CT device, to which the invention is not restricted however. Located in the gantry housing C6 is a closed gantry not shown in the diagram on which are arranged a first X-ray tube C2 with a detector C3 lying opposite it. Optionally arranged in the CT system shown here are a second X-ray tube C4 and a detector C5 lying opposite it, so that a higher temporal resolution can be achieved by the radiator/detector combination additionally available, or with the use of different X-ray energy spectra in the radiator/detector system, dual-energy examinations can be undertaken.

The CT system C1 also comprises a patient couch C8 on which the patient can be pushed during the examination along a system axis C9, also referred to as the z axis, into the measurement field, with the scanning itself able to occur both as a pure orbital scan without forward movement of the patient exclusively in the region of interest under examination. The movement of the patient couch C8 relative to the gantry is effected by a suitable motorization. In this case the X-ray source C2 or C4 respectively rotates around the patient. In such cases the detector C3 or C5 respectively moves in parallel in relation to the X-ray source C2 or C4 in order to record projection measurement data which is then used for reconstruction of picture slices. As an alternative to a sequential scan in which the patient is pushed step-by step between the individual scans through the examination field, there is naturally also the option provided of a spiral scan, in which the patient is pushed continuously during the orbital scanning with the X-rays along the system axis C9 through the examination field between X-ray tube C2 or C4 respectively and detector C3 or C5 respectively. The movement of the patient along the axis C9 and the simultaneous orbital movement of the X-ray source C2 or C4 respectively produces a helical track for a spiral scan for the X-ray source C2 or C4 relative to the patient during the measurement. This track can also be achieved by the gantry being moved along the axis C9 while the patient does not move. It is also possible to move the patient continuously and periodically backwards and forwards between two points.

The CT system 10 is controlled by a control and processing unit C10 with a computer program code $Prg_1$ through $Prg_n$ present in a memory. It should be noted that these computer program codes $Prg_1$ to $Prg_n$ can naturally also be contained on an external storage medium and loaded in the control and processing unit C10 as required.

From the control and processing unit C10 acquisition control signals AS can be transmitted via a control interface 24 in order to control the CT system C1 in accordance with specific measurement protocols. The acquisition control signals AS relate in such cases to the X-ray tubes C2 and C4, with specifications able to be given about their power and the times at which they are switched on and switched off, as well as the gantry, with specifications able to be provided about their speed of rotation as well as the advance of the couch.

Since the control and processing unit C10 has an input console, measurement parameters can be entered by a user or operator of the CT device C1 which then control the data recording in the form of acquisition control signals AS. Information about measured parameters currently used can be shown on the screen of the control and processing unit C10; in addition further information relevant for the operator can be displayed.

The projection measurement data p or raw data acquired by detector C3 or C5 is transferred via a raw data interface C23 to the control and processing unit C10. This raw data p is then, if necessary after suitable pre-processing, further processed in a picture reconstruction component C21. The picture reconstruction component C21 is realized in this exemplary embodiment in the control and processing unit C10 in the form of software on a processor, e.g. in the form of one or more of the computer program codes $Prg_1$ through $Prg_n$, or code segments. What has already been stated in relation to the control of the measurement process applies in relation to picture reconstruction, that the computer program codes $Prg_1$ to $Prg_n$ or code segments can also be contained on an external storage medium and can be loaded if necessary into the control and processing unit C10. It is also possible for the control of the measurement process and the picture reconstruction to be carried out by different processing units.

The picture data f reconstructed by the picture reconstruction component C21 is then stored in a memory C22 of the control and processing unit C10 and/or output in the usual way on the screen of the control and processing unit C10. It can also be fed via an interface not shown in FIG. 1 into a network connected to the computed-tomography system C1, for example a radiological information system (RIS) and stored in mass storage accessible in this system or output as pictures.

The control and processing unit C10 can additionally also execute the function of an EKG, with a line C12 for deriving the EKG potentials between patient and control and processing unit C10 being used. In addition the CT system C1 shown in FIG. 1 also has a contrast media injector C11 via which additional contrast media is injected into the blood circulation of the patient so that the blood vessels of the patient, especially the heart chambers of the beating heart, can be better represented. In addition there is also the opportunity of carrying out perfusion measurements for which the suggested method is likewise suitable.

Figure 2:
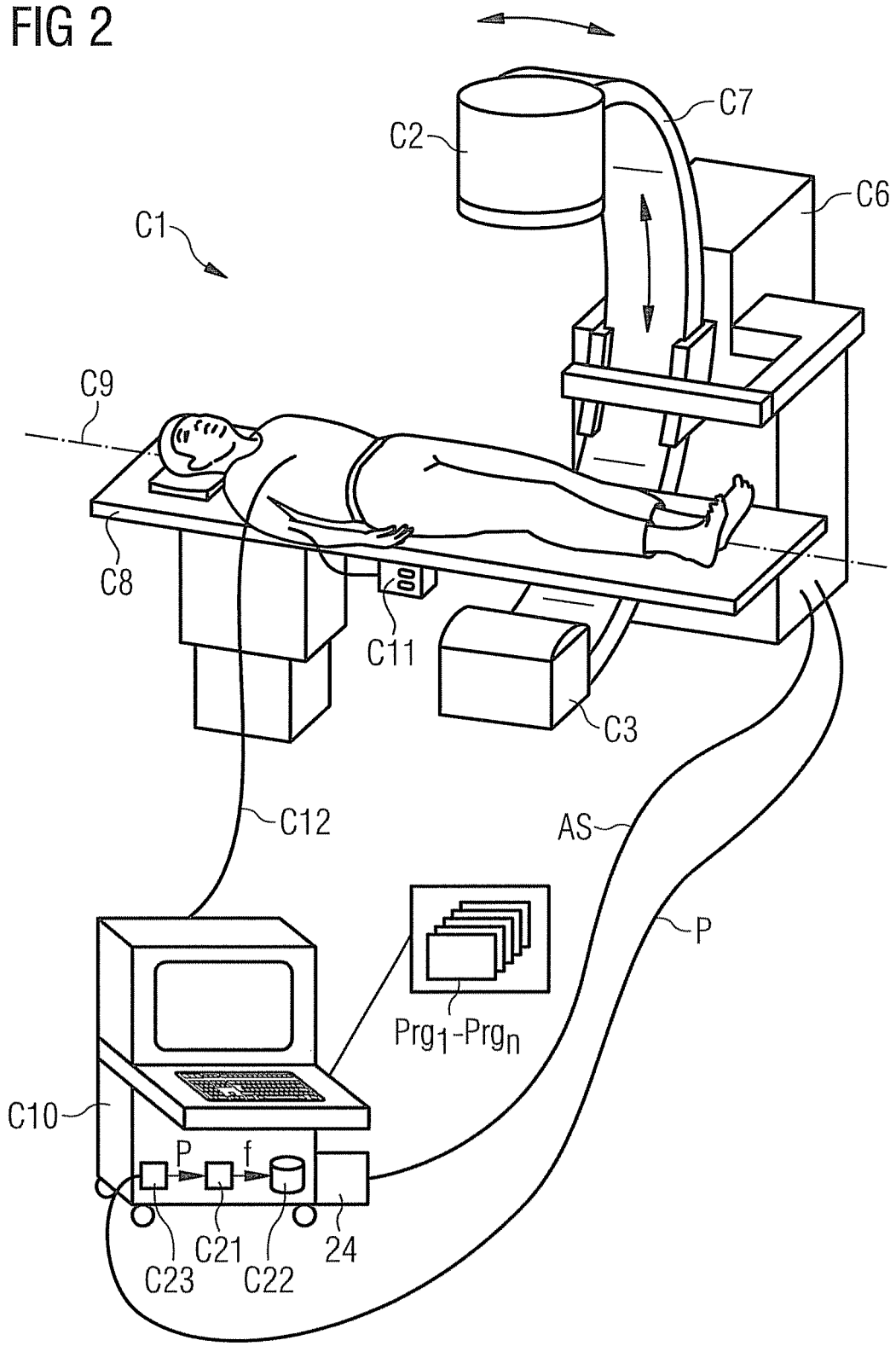
FIG. 2: a second schematic diagram of an example embodiment of a computed tomography system with a picture reconstruction component.

FIG. 2 shows a C-arm system, in which, by contrast with the CT system of FIG. 1, the housing C6 carries the C-arm C7, to one side of which is attached the X-ray tube C2 and to the opposite side the detector C3. The C-arm C7 is likewise hinged around a system axis C9 for a scan, so that a scan can be undertaken from a plurality of scanning angles and corresponding projection data p can be determined from a plurality of projection angles. The C-arm system C1 of FIG. 2, like the CT system from FIG. 1, has a control and processing unit C10 of the type described for FIG. 1.

An embodiment of the invention is able to be used in both of the systems shown in FIGS. 1 and 2. Furthermore it is basically also able to be used for other CT systems, e.g. for CT systems with a detector forming a complete ring.

Where pictures are to be recorded of parts of a patient's body which do not move or can be kept still, there are no significant problems with movement artifacts for recording the projections and for the subsequent picture reconstruction. By contrast, this situation is critical for moving objects under examination. The situation is considered below in which a CT picture of a moving object under examination is to be recorded.

An example of an object under examination which moves periodically is the human heart. An embodiment of the invention will be explained below in greater detail with reference to cardio CT, i.e. a CT picture of the beating heart. Naturally it is not restricted to this application.

It is well known that the human heart carries out periodic movements. The periodic movement consists in this case of an alternating sequence or a rest or sleep phase and a movement or beating phase. The rest phase has a duration of usually between 500 to 800 ms, the beating phase has a duration of 200 to 250 ms.

Figure 3:
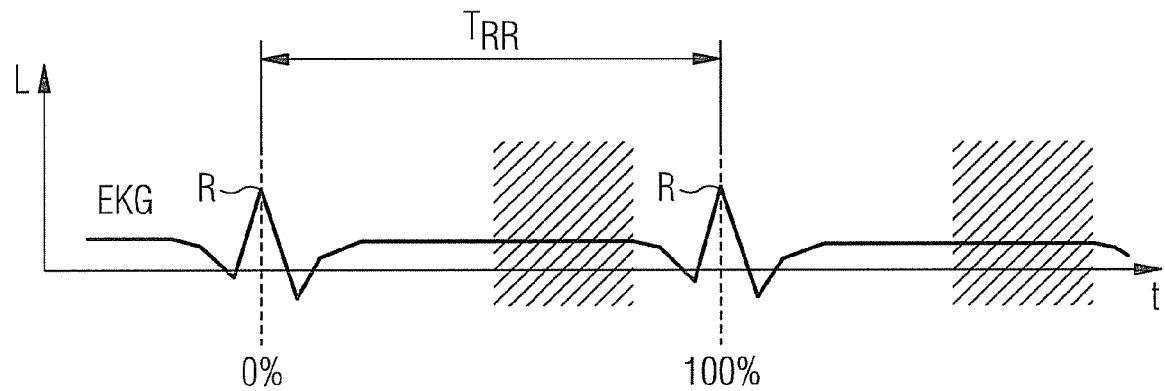
FIG. 3: a number of consecutive heart cycles.

This can be seen from FIG. 3, in which the level L of the EKG signal labeled EKG of a patient is plotted over the time t. The EKG signal illustrates the periodic movement of the heart of the patient, with the beginning of a heart cycle being determined by R wave R and the duration of the respective heart cycle by the RR interval $T_{RR}$, i.e. by the distance between the R wave R initiating the heart cycle and the R wave R initiating the following heart cycle. A heart phase starts with an R wave R at 0% and ends at the next R wave R at 100%. The conversion between the dimension of the time and the heart phase is possible at any time; EKG data can be used for this purpose, which indicates at any given point in time which heart phase is actually present. The rest phase of the heart, i.e. the phase of minimal heart movement, is indicated by dashed lines in each case.

In heart imaging by way of CT the heart phase during which the data is recorded is decisive for a good picture quality. An attempt is thus usually made to use data for the picture reconstruction which was recorded during a heart phase with little or minimal heart movement.

As well as the existing requirements relating to the quality of CT pictures for objects under examination which do not move, there is the objective with heart recordings of achieving a high temporal resolution of the pictures. The temporal resolution in this case is inversely proportional to the period of time which is needed for detecting the projections. The more time elapses during the data recording the more the heart moves during this measurement time. This movement leads to undesired movement artifacts in the CT pictures. The expressiveness of the CT is drastically reduced by this.

For CT picture reconstructions with measurements in parallel beam geometry a data interval, i.e. a series of consecutive projections, with each projection corresponding to a measurement at a specific angle of projection, must be available which corresponds to at least one half orbit of the X-ray source around the object under examination, i.e. a projection angle range of 180°. With a cone beam geometry the projection angle range must amount to 180° plus the cone opening angle. Both cases are summarized below under the designation "data of a half orbit". This minimum data interval is necessary to be able to reconstruct each pixel in the measurement field. In the center of rotation a projection angle range of 180° is also sufficient in cone beam geometry. The best possible temporal resolution in a CT picture reconstructed in this way thus amounts in the vicinity of the center of rotation to precisely half the rotation time of the CT device.

The desired improved temporal resolution for the cardio CT can be achieved by a reduction in the rotation time of the CT devices. The fastest rotation time of a single-tube CT device amounts to approximately 0.27 seconds according to the prior art, corresponding to a best possible temporal resolution of 135 ms. A reduction in the rotation time is however mechanically complex and expensive, which is why this represents a limiting factor in the construction of low-cost CT devices.

With so-called multisegment reconstruction an attempt is made to improve the temporal resolution by combination of data from a number of consecutive heartbeats. The basis of these methods is to record projections of the same position of the object under examination in a number of heart cycles in order to subsequently combine suitable parts of the data for the picture reconstruction. Thus for example data from a projection angle range of between 0°-90° can be used from a first heart cycle and data from a projection angle range of 90°-180° can be used from a second heart cycle. The time resolution corresponds in the said example to the period of time needed for a rotation by 90°. Other divisions are also possible, for example a range of 0-120° from a first heart cycle and 120-180° from a second heart cycle. Instead of two heart cycles more heart cycles can also of course be considered. Overall a complete dataset is thus available by combining the data from the different heart cycles. It should be noted that the number of projection angle ranges should each belong approximately to the same heart phase of the heart cycle, e.g. to the heart phase between 60 and 80%. This guarantees that the different data maps the same state of the heart in each case, by which movement artifacts can be avoided.

Multisegment reconstruction is described for example in

Flohr T, Ohnesorge B; Heart rate adaptive optimization of spatial and temporal resolution for electrocardiogram-gated multislice spiral CT of the heart. J Comput Assist Tomogr 2001; 25:907-923, the entire contents of which are hereby incorporated herein by reference;

Ohnesorge B B C, Flohr T, Reiser M F. Multi-slice CT in cardiac imaging: technical principles, clinical application, and future developments. Berlin, Germany: Springer Verlag, 2002, the entire contents of which are hereby incorporated herein by reference;

Taguchi K., Anno H. High temporal resolution for multi-slice helical computed tomography, Med. Phys. 2000, 27 (5): 861-872, the entire contents of which are hereby incorporated herein by reference;

Anno H., Kato R., Katada K. et al, Improvement of temporal resolutions in ECG-gated CT-Coronary angiography using a 0.4 sec/Rotation multi-slice helical CT system, Radiology 2001 (221): 201-210, the entire contents of which are hereby incorporated herein by reference;

Lembcke A., Rogalla P., Blobel J., Segment-Rekonstruktion: Ein neues Verfahren für die kardiologische Diagnostik, (Segment reconstruction: A new method for cardiological diagnostics) VISIONS(ISSN 1617-2876) 5/2001: 52-55, the entire contents of which are hereby incorporated herein by reference; and Flohr T., Bruder H., Stiersdorfer K., Simon J., Schaller S., Ohnesorge B., New Technical Developments in Multislice CT, Part 2:
Sub-Millimeter 16-Slice Scanning and Increased Gantry Rotation Speed for Cardiac Imaging, contd. Röntgenstr. 2002; 174: 1022-1027, the entire contents of which are hereby incorporated herein by reference.

A disadvantage of multisegment reconstruction is that the multiple scanning is associated with an increased dose for the patient. The system must either operate with a spiral CT recording with very small pitch or patient table advance or, for sequence CT recording, data must be recorded at the same position during the duration of a number of heartbeats. If a bisegment reconstruction is used, i.e. if the data of two heart cycles is combined, this produces a radiation dose increased by a factor of two as a rule.

The increased radiation dose resulting from the previously used multisegment reconstruction serves exclusively to improve the temporal resolution. In particular the noise in the CT pictures is not lessened by it. This absence of effect on the picture noise despite a greatly increased radiation dose is a major disadvantage of multisegment approaches so that attempts are made to restrict its use to heart rates which are greatly increased and not able to be reduced by medication.

Figure 4:
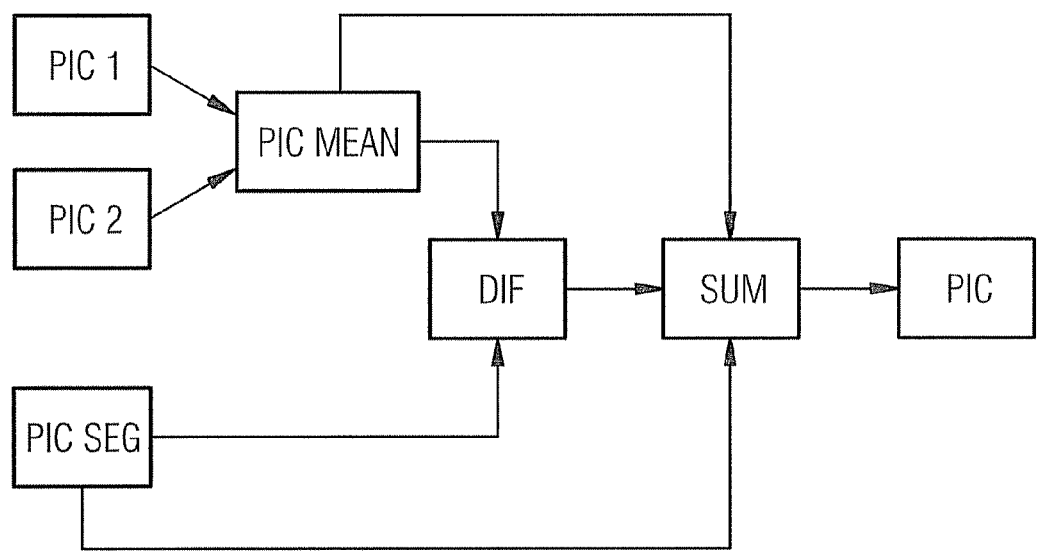
FIG. 4: a flow diagram.

An improved option of multisegment picture reconstruction is described below with reference to the flow diagram of FIG. 4. The projections are initially recorded in the known way with data being recorded during at least two heart cycles in relation to each segment of the heart to be pictured. It is assumed for the sake of simplification below that data of two heart cycles is available. The procedure explained is however able to be transferred accordingly to a larger number of heart cycles.

Two CT pictures, PIC 1 and PIC 2 will be reconstructed from the measurement data. The first picture, PIC 1, involves a picture which has been reconstructed on the basis of a complete dataset, i.e. the data of a half orbit of the first heart cycle. The second picture, PIC 2, is a picture which has been reconstructed based on a complete dataset, i.e. the data of a half orbit, of the second heart cycle. From these two pictures PIC 1 and PIC 2 a mean picture PIC MEAN is calculated. This is done by pixel-by-pixel addition and halving of the picture values of pictures PIC 1 and PIC 2. With an N-segment reconstruction, by forming such a mean value, the noise in the resulting mean value picture PIC MEAN is reduced in relation to the original pictures by the factor $\sqrt{N}$, in the present example of a reconstruction therefore by the factor $\sqrt{2}$.

In addition a picture PIC SEG is computed from the data of the two heart cycles in accordance with the known multisegment reconstruction. For reconstruction of the picture PIC SEG data from the two heart cycles is combined so that a complete dataset is available. The picture PIC SEG is characterized by an enhanced temporal resolution compared to pictures PIC 1, PIC 2 and PIC MEAN.

Figure 5A:
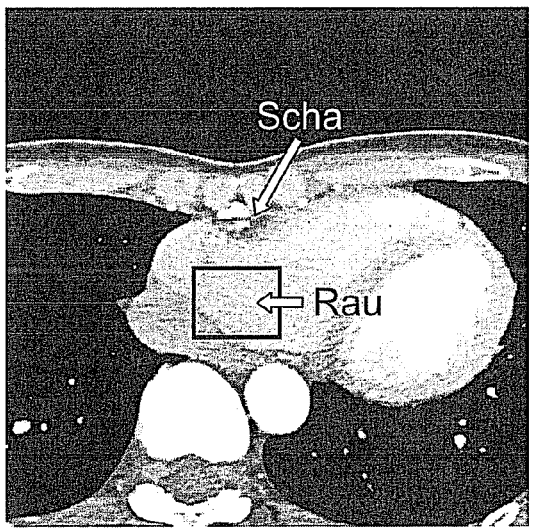
FIG. 5: two CT pictures of the heart.
Figure 5B:
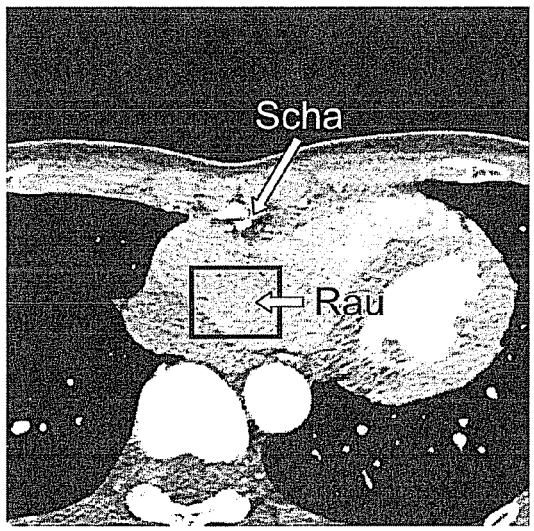

Examples for pictures PIC MEAN and PIC SEG are shown in FIG. 5, with FIG. 5A showing a picture PIC MEAN and FIG. 5B showing a picture PIC SEG. The region indicated by the letters Scha (sharpness) and an arrow corresponds to the central part of the right-hand coronary artery. This involves a region of the heart in which movement takes place. It can be clearly seen that the sharpness of the mean value picture of FIG. 5A in this region is much less than that of the multisegment picture of FIG. 5B with the better temporal resolution.

On the other hand the noise is reduced by the mean value formation, which is not the case with the multisegment picture. This is especially apparent in the region indicated by the letters Rau (noise): in FIG. 5B there is greatly increased noise by comparison with FIG. 5A. This point shows a tissue area (muscle area) of the right-hand heart chamber.

In summary it can thus be established through a comparison of the pictures PIC MEAN and PIC SEG that the advantage of the picture PIC MEAN is the reduce noise as a result of the accumulation of the dose from the recordings of the number of heart cycles, while the advantage of picture PIC SEG is the increased temporal resolution.

Figure 6A:
FIG. 6: Difference diagrams between the two CT pictures of FIG. 5, FIG. 7: an improved CT picture based on the CT pictures of FIG. 5 using the difference of FIG. 6.

The amount of the difference of the pixel values is now computed pixel-by-pixel from the two pictures PIC MEAN and PIC SEG. This difference is processed, as explained in greater detail below, so that finally a difference picture DIF results. An example of this type of difference picture DIF, which results from the comparison of the two pictures of FIG. 5, is shown in FIG. 6A. The brighter is the pixel in the difference picture DIF of FIG. 6A, the greater is the difference between the pictures PIC MEAN and PIC SEG at this point. This difference indicates the degree of movement at the respective point. This is based on the fact that the mean value picture PIC MEAN specifies a mean state of the heart over a number of heart phases of the heart cycle, while the picture PIC SEG corresponds to a specific heart phase or to a smaller segment of heart phases of the heart cycle.

The specified processing of the difference to achieve the difference picture DIF consists of different amount values below a first threshold T1, e.g. T1=40 HU, having been set to 0, and different amount values greater than a second threshold T2, e.g. T2=80 HU, being set to T2. The reason for using the first threshold is that small deviations between the pictures PIC MEAN and PIC SEG merely originate from noise and not from an actual movement. These deviations should not be taken into consideration below. By using the second threshold the differences are restricted upwards. The reason for this lies in the fact, that movements of great contrasts, e.g. of lung tissue to air, should not be more greatly considered and other movements, e.g. of contrasts between iodine-filled vessels and tissue.

The thresholds T1 and T2 can for example be determined by including a histogram representation. Thus the first threshold T1 can be obtained for example by demanding that a specific percentage, e.g. 75%, of all difference values are based on a movement and the remaining 25% of the difference values are caused by noise. The second threshold T2 can be obtained in a similar fashion, by demanding that a specific percentage, e.g. 15%, of all difference values should lie above the second threshold.

Figure 6B:

The difference picture DIF is also subjected to lowpass filtering before its further use so that a soft transition between the components with a different amount of movement is guaranteed. To improve the result a non-linear spreading of the difference values, e.g. by means of an exponential function, can be executed before the lowpass filtering and the corresponding despreading executed accordingly after the lowpass filtering. Subsequently another restriction of the range of values of the modified difference picture DIF is undertaken by the values being scaled accordingly. The result of this processing in the form of a modified difference picture DIF is shown in FIG. 6B.

The object of determining the difference picture DIF is to identify local regions within the CT pictures in which a heart movement is present. These regions are enlarged by the transition from FIG. 6A to FIG. 6B. In this way a type of edge of a number of pixels is "added in" around each measured difference to insure that the region concerned is recognized safely and comprehensively as a moving region. As will be shown below, the temporally highly-resolved picture should be used for these regions. If for example smaller vessels only partly overlap in the difference the widening of the moved region should insure that in the subsequent merging the vessel can still be completely detected from the temporally highly-resolved picture.

Subsequently in the step SUM of FIG. 4, a merging of the pictures PIC MEAN and PIC SEG takes place, with the modified difference picture DIF being used as a weighting factor. The pixel-by-pixel merging of the mean picture PIC MEAN and the temporally highly-resolved picture PIC SEG with the difference picture DIF as a weighing picture for determining the result picture PIC occurs in the following form:

$$PIC_i = PIC\ MEAN_i \cdot (1-DIF_i) + PIC\ SEG_i \cdot DIF_i$$

The index i stands for the respective picture pixel in this case.

The maximum value for a pixel of the difference picture DIF amounts to 1. This corresponds to a large movement. In this case $PIC_i = PIC\ SEG_i$ applies, i.e. the pixel value of the temporally highly-resolved picture PIC SEG is accepted. The minimum value for a pixel of the difference picture DIF amounts to 0. This corresponds to no movement. In this case the following applies:
$PIC_i = PIC\ MEAN_i$, i.e. the pixel value of the mean value picture PIC MEAN is accepted. For values of the difference picture DIF between 0 and 1, both the temporally highly-resolved picture PIC SEG and also the mean value picture PIC MEAN contribute to the result picture PIC.

Figure 7:
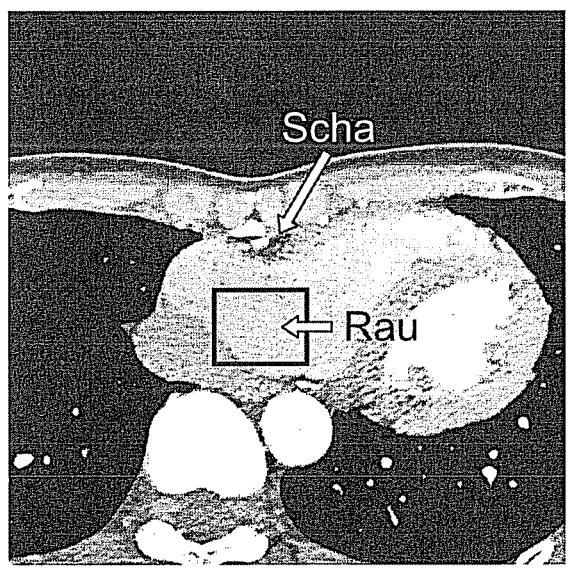

An example of a result picture PIC which has been computed from the pictures of FIGS. 5 and 6, is shown in FIG. 7. It can be seen that the result picture PIC is characterized by a high level of sharpness in moved areas—such as also indicated in FIG. 5 by the letters Scha and the arrow. This corresponds to the advantage of the temporally highly-resolved picture PIC SEG. The result picture PIC is also characterized in regions with little movement by a reduced noise, as can be seen in FIG. 5 in the region labeled by the letters Rau. This corresponds to the advantage of the mean picture PIC MEAN. Overall a sharp picture with low noise in non-moving regions is thus produced.

The described procedure thus enables the known advantage of multisegment reconstruction to be used, namely the avoidance of movement artifacts as a result of increased temporal resolution. Above and beyond this the high-dose exposure for the patient is efficiently utilized in that noise is drastically reduced compared to the conventional multisegment reconstruction. The increased dose thus serves two purposes: increasing the time resolution while simultaneously improving the picture noise.

Conversely the procedure can also be as follows: the intensity of the X-radiation during data recording is greatly reduced compared to conventional measurement for a multisegment reconstruction, e.g. to 60-70%. If the dose is reduced by a factor of N during an N-segment reconstruction, this reconstruction would be dose-neutral compared to a mono-segment reconstruction in relation to picture noise. In this case it is still possible to obtain CT pictures with high temporal resolution, the noise of which is not worsened compared to a one-time measurement with 100% of the radiation intensity. This means that it is thus possible to carry out a multi-segment reconstruction without exposing the patient to an increased radiation dose compared to a simple measurement or to an only slightly increased radiation dose.

Previously the embodiment has been described in which the difference picture DIF is determined by comparing the mean value picture PIC MEAN and the picture PIC SEG. In this case two pictures with different temporal resolution serve to determine the movement information. By contrast it is also possible to obtain the difference picture DIF by comparing two pictures with the same temporal resolution. The two pictures PIC 1 and PIC 2 are suitable for this for example.

The invention has been described above using an exemplary embodiment. It goes without saying that numerous changes and modifications are possible without departing from the framework of the invention.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, non-transitory computer readable medium and non-transitory computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a non-transitory computer readable medium and is adapted to perform any one of the aforementioned methods when run on a computer device (a device including a processor). Thus, the non-transitory storage medium or non-transitory computer readable medium, is adapted to store information and is adapted to interact with a data processing facility or computer device to execute the program of any of the above mentioned embodiments and/or to perform the method of any of the above mentioned embodiments.

The non-transitory computer readable medium or non-transitory storage medium may be a built-in medium installed inside a computer device main body or a removable non-transitory medium arranged so that it can be separated from the computer device main body. Examples of the built-in non-transitory medium include, but are not limited to, rewriteable non-volatile memories, such as ROMs and flash memories, and hard disks. Examples of the removable non-transitory medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. Method for reconstruction of picture data of a cyclically moving object from measurement data, the measurement data having been recorded for a relative rotation movement between a radiation source of a computed tomography system and the object under examination during a plurality of movement cycles of the object under examination, the method comprising:
    determining a first picture and a second picture from the measurement data, with measurement data of different movement cycles being combined into a measurement dataset on which to base the picture reconstruction for reconstruction of the second picture,
    computing difference information by a comparison of the first picture with the second picture; and
    computing a result picture using the difference information from the first picture and the second picture, wherein, to compute the result picture pixel-by-pixel, a weighted sum is directly formed from the first picture and the second picture, with the weighting depending on the difference information.

2. The method as claimed in claim 1, wherein, to determine the first picture, at least one third picture and one fourth picture are reconstructed, with the third picture being reconstructed from data of a first movement cycle and the fourth picture from data of a second movement cycle, and the first picture being determined by forming the mean values from at least the third picture and the fourth picture.

3. The method as claimed in claim 1, wherein a multisegment reconstruction method is employed to determine the second picture.

4. The method as claimed in claim 1, wherein the first and the second picture have different temporal resolutions from each other.

5. The method as claimed in claim 1, wherein, to compute the difference information, a difference picture is determined by pixel-by-pixel formation of the difference between the first picture and the second picture.

6. The method as claimed in claim 5, wherein the values of the difference picture below a first threshold value are set to zero.

7. The method as claimed in claim 6, wherein the values of the difference picture above a second threshold value are set to the second threshold value.

8. The method as claimed in claim 6, wherein the difference picture is subjected to a lowpass filtering.

9. The method as claimed in claim 5, wherein the values of the difference picture above a second threshold value are set to the second threshold value.

10. The method as claimed in claim 5, wherein the difference picture is subjected to a lowpass filtering.

11. The method as claimed in claim 10, wherein the difference picture is subjected to a non-linear noise removal before the lowpass filtering.

12. A non-transitory computer readable medium including program segments for, when executed on a computer device, causing the computer device to carry out the method as claimed in claim 1.

13. A computer program product, comprising program code segments of a computer program stored on a non-transitory computer-readable data carrier to execute the method as claimed in claim 1 when the computer program is executed on a computer.

14. A method for reconstruction of picture data of a cyclically moving object from measurement data, the measurement data having been recorded for a relative rotation movement between a radiation source of a computed tomography system and the object under examination during a plurality of movement cycles of the object under examination, the method comprising:
    determining a first picture and a second picture from the measurement data, the first picture is reconstructed from data of a first movement cycle to calculate the difference information, the second picture being reconstructed from data of a second movement cycle;

computing difference information by a comparison of the first picture with the second picture;

determining a mean value picture from the first and the second picture; and computing a result picture using the difference information and a third picture, the third picture being based on the data of the first movement cycle and the data of the second movement cycle, wherein, to compute the result picture pixel-by-pixel, a weighted sum is directly formed from the first picture and the second picture, with the weighting depending on the difference information.

15. A control and processing unit for reconstruction of picture data of an object under examination from measurement data of a CT system, comprising:

a program memory for storage of program code, the program code being present in the program memory and carrying out, when executed,
determining a first picture and a second picture from the measurement data, with measurement data of different movement cycles being combined into a measurement dataset on which to base the picture reconstruction for reconstruction of the second picture,
computing difference information by a comparison of the first picture with the second picture, and
computing a result picture using the difference information from the first picture and the second picture, wherein, to compute the result picture pixel-by-pixel, a weighted sum is directly formed from the first picture and the second picture, with the weighting depending on the difference information.

16. A CT system comprising a control and processing unit as claimed in claim 15.

* * * * *